United States Patent
Rus et al.

(10) Patent No.: US 7,321,385 B2
(45) Date of Patent: Jan. 22, 2008

(54) SURGICAL LIGHTING CONTROL AND VIDEO SYSTEM

(75) Inventors: Steven H. Rus, Chardon, OH (US); Terry A. Drabinski, Stow, OH (US); James A. Petrucci, Chesterland, OH (US); David Jesurun, South Euclid, OH (US); Alan J. Greszler, Elyria, OH (US); Yury Keselman, Beachwood, OH (US)

(73) Assignee: Steris Inc., Temecula, CA (US)

( * ) Notice: Subject to any disclaimer, the term of this patent is extended or adjusted under 35 U.S.C. 154(b) by 918 days.

(21) Appl. No.: 10/342,540

(22) Filed: Jan. 15, 2003

(65) Prior Publication Data

US 2003/0142204 A1 Jul. 31, 2003

Related U.S. Application Data

(60) Provisional application No. 60/348,999, filed on Jan. 15, 2002.

(51) Int. Cl.
*H04N 7/18* (2006.01)

(52) U.S. Cl. .............. 348/69; 348/77; 348/68; 348/135; 348/370; 348/373; 348/143; 600/249; 600/248; 362/395; 362/804; 362/399

(58) Field of Classification Search .......... 348/69, 348/77, 135, 373, 370, 68, 143; 362/399, 362/395, 804; 600/249, 248
See application file for complete search history.

(56) References Cited

U.S. PATENT DOCUMENTS

| | | | |
|---|---|---|---|
| 5,061,997 A | 10/1991 | Rea et al. | |
| 5,526,245 A | 6/1996 | Davis et al. | |
| 5,803,905 A | 9/1998 | Allred et al. | |
| 5,994,844 A * | 11/1999 | Crawford et al. | ........... 315/151 |
| 6,132,062 A | 10/2000 | Borders et al. | |
| 6,160,582 A | 12/2000 | Hill | |
| 6,402,351 B1 * | 6/2002 | Borders et al. | ............. 362/395 |
| 6,639,623 B2 * | 10/2003 | Howell et al. | ................ 348/61 |

FOREIGN PATENT DOCUMENTS

| | | |
|---|---|---|
| DE | 196 11 161 A1 | 9/1997 |
| EP | 1 107 422 A2 | 6/2001 |
| GB | 2 176 640 A | 12/1986 |

OTHER PUBLICATIONS

International Search Report for International Application No. PCT/US03/01138; Date of actual Search completion- Dec. 8, 2003.

* cited by examiner

*Primary Examiner*—Shawn S. An
(74) *Attorney, Agent, or Firm*—Fay Sharpe LLP (57) ABSTRACT

A surgical light system (10) includes a lighthead (44) coupled to a suspension arm (41') adapted for mounting to a surface (14) of a surgical room. A bulb (130) is disposed in the lighthead. A processor (120) in the lighthead is operatively coupled with the bulb for controlling an intensity of light of the bulb and is adapted to generate a lighthead status signal representative of a first status of the lighthead. A control apparatus (32, 34) is in operative communication with the processor (120) in the lighthead. The control apparatus receives the lighthead status signal and selects a set of control algorithms from among a group of algorithms based on the lighthead status signal for controlling the lighthead. The lighthead status signal includes information regarding a size of the lighthead, an intensity of light from the bulb, a condition of the bulb, a level of current applied to the bulb, a level of current applied to the bulb, a level of voltage applied to the bulb, an internal temperature of the lighthead, and the presence of one or more of a video camera, a surgical task light, and a controllable ambient light. A human-readable display device (160) is provided for displaying information relating to the lighthead status signal. Several levels of redundancy are provided in the control system to minimize the potential loss of control due to failures. In that regard, the lightheads are operable when the control apparatus (32, 34) fails.

16 Claims, 7 Drawing Sheets

SURGICAL LIGHTING CONTROL AND VIDEO SYSTEM

CROSS-REFERENCE TO RELATED APPLICATION

This application claims the benefit of U.S. provisional application Ser. No. 60/348,999, filed Jan. 15, 2002.

BACKGROUND OF THE INVENTION

The present invention relates to the surgical lighting, table, and accessory arts, and, more particularly, to a surgical lighting control system providing multiple user interfaces, centralized graphical control for various functions, advanced camera detection/signal routing, and closed loop control of lamp intensity. It finds particular application in conjunction with providing a comprehensive control system for a surgical operating room (OR) theater and will be described with particular reference thereto. It is to be appreciated, however, that the invention also finds application in other multi-task control applications and is not limited to the aforementioned operating room environment.

Typically, in an operating room setting, large, high lumen output lightheads are used to illuminate the surgical site. Often, video cameras, are attached to the lightheads for documenting the surgery, and to assist the surgeon in achieving more optimal views. Some systems offer no control of the camera to personnel in the OR. Without physically moving the camera/lighthead, such systems only offer a single camera orientation and zoom factor. Other systems offer control of the camera and lightheads to personnel in the OR, but not to the surgeon. The surgeon must request that a non-sterile circulating nurse adjust the lighting controls or the camera controls when needed.

Existing systems do not monitor power delivered to the bulbs within the lighthead. This results in light intensity fluctuations due to bulb deviations, voltage fluctuations, and line resistences. Variances in the lamp power can reduce light intensity with potential adverse effects on the surgical procedure or increase light intensity causing a reduced lamp life.

Additionally, most existing systems do not offer centralized control. Accordingly, the circulating nurse staff must move first to one panel to operate light intensity controls, then to another location to rotate the camera, etc. This leads to confusion when operating the systems, and clutter in the OR due to additional user interface locations.

In systems using a centralized control, hardware updates/upgrades are difficult because the software of the control often cannot be adapted to recognize and operate with the new equipment. It would be desirable to provide a surgical lighting and video control system with software adapted to interact with new equipment through simple software parameter updates or settings.

The present invention provides new and improved methods and apparatus that overcome the above referenced problems and others to provide better, more comprehensive control of lighting and video systems in surgical operating room applications.

BRIEF SUMMARY OF THE INVENTION

The preferred embodiments of the present invention provide a plug and play control interface that gives a user access to multiple devices at one station, gives the surgeon control of more devices within the sterile field, and makes control of the system simpler and more intuitive.

The present invention improves user access to the system by providing a graphical LCD display for use to control a plurality of devices, such as overhead lighting, ambient lighting, cameras, and other operating room accessories. The surgeon's control is improved by a voice interface system, allowing the surgeon to adjust lighting and other aspects by simply speaking. A foot pedal interface and an infra-red remote control interface grant the surgeon control of the cameras, enabling direct control of rotate and zoom functions of the camera.

The preferred embodiments of the present invention provide plug and play compatibility, so that devices such as cameras, entire lightheads, task lights, and other surgical accessories can be switched in and out of the system as needed, without the need to update system software or control protocol. This may occur as additional lightheads or other devices are added to the system or when devices are replaced as by way of an upgrade or the like.

A wall control unit of the subject system provides a graphical LCD display that enables centralized user input/output for all controls. The wall control also provides input/output connections for system options such as a video, recording device, voice control, a fiber-optic task light, and camera foot control. The LCD interface provides high-level user control of the video camera fiber optic task light, ambient light, and multiple lightheads.

All medium and large sized lightheads are preferably camera ready. A camera module can be placed into any of these lightheads as desired. The control system is adapted to automatically detect the particular lighthead in which the camera is located and direct the signal to the wall control through electronic means in a "plug and play" fashion.

Further, service function is incorporated into the system that allows service or maintenance personnel to disconnect entire lightheads for replacement with new lightheads. The control system detects a new lighthead and downloads compatible software to the lighthead (plug and play) as necessary. This decreases product down time due to service calls. Each lighthead includes a micro-controller adapted to send and receive control information from the wall control and further adapted to respond to the switches on the light handle bezel.

The micro-controller also provides closed loop control for tight control over lamp power. The controller measures lamp voltage and current and sets a duty cycle for a pulse width modulation (PWM) circuit. This effectively gives consistent light by compensating for most all sources of variation.

The advanced control allows all lightheads in the system to be turned on/off from the switch bezel input on any light in the system. Pushing and holding the '−' intensity down button at the bezel of the lighthead handle for a selected period, preferably four (4) seconds turns all lightheads off and preferably simultaneously turns an ambient light on. Pushing and holding the '+' intensity up button a selected period preferably for two (2) seconds turns all the lightheads on and preferably simultaneously turns the ambient light off.

The wall control provides a simple, centralized user interface saving time for the circulating nurse. The advanced control of the switches on the light handle bezel gives control of the lights to the surgeon as well. This saves time for the entire staff.

The control system provides several levels of redundancy in order to minimize the potential loss of control of the lighting system during surgical procedures. Either one of the two power supplies in the control center is sufficient to maintain operation of the microcontroller. If the microcontroller or switches in the wall control unit fail, then ON/OFF and intensity control functionality can be performed using just the lighthead-based microcontroller and switches.

Video camera features are accessible through the user interface, including at least power and zoom, rotate, brightness and focus controls. Advanced camera controls are also accessible through the user interface including white balance, picture freeze, time and date display as examples. The camera module is adapted for connection with any medium or large lighthead. The control system of the subject system automatically detects camera module presence and directs the video signal(s) to the wall control.

Many control features are provided in the surgical lighting system according to the invention. A graphical user interface, preferably, a LCD display provides for centralized control of all components in the system. ON/OFF control of all lightheads is provided in the system from a single point of intensity control at the light handle switch bezel while maintaining sterile technique. Advanced camera control features are provided including white balance, picture freeze, time and date display. The control system detects the camera module and directs the video signal to the wall control. This coincides with the system's ability to accept a camera module at multiple locations. A closed-loop lamp power control scheme maintains consistent intensity levels over time and over differing installation conditions. The wall control senses new lightheads and automatically download software to make the lighthead compatible in the system.

The above list is not exhaustive of the control features provided in the surgical lighting systems according to the invention.

BRIEF DESCRIPTION OF THE DRAWINGS

The invention may take form in certain methods, parts, and arrangements of parts, the preferred embodiments of which will be described in detail in this specification and illustrated in the accompanying drawings which form a part hereof and wherein.

DETAILED DESCRIPTION OF THE PREFERRED EMBODIMENTS

Figure 1:
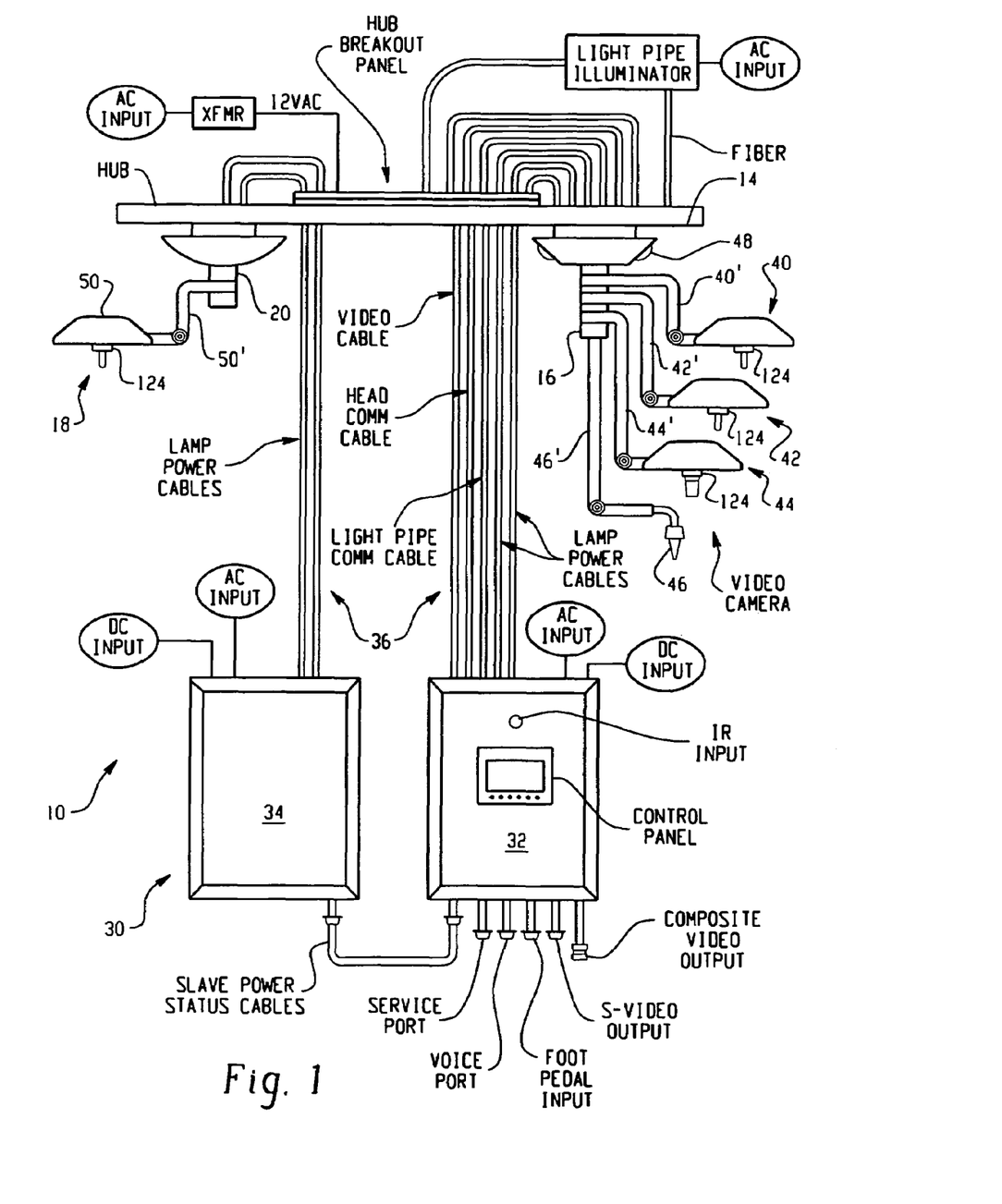
FIG. 1 is a perspective view of a surgical light system in accordance with the present invention showing a first set of surgical lighting equipment suspended from a primary spindle and a second set of lighting equipment suspended from a secondary spindle, and a system control apparatus.

With reference now to the drawing figures wherein the showings are purposes of illustrating the preferred embodiments of the invention only and not for purposes of limiting same, FIG. 1 shows a surgical lighting system 10 including a first set of lighting devices 12 supported from the ceiling 14 of an operating room by a primary spindle hub 16 and a second set of lighting devices 18 supported at the ceiling 14 by a secondary spindle hub 20. A lighting control apparatus 30 includes a master control unit 32 for operating the first set of lighting devices 12 and a second control unit 34 for controlling operation of the second set of lighting devices 18. A set of communication and power lines 36 connect the lighting control apparatus 30 with the first and second set of lighting devices 12, 18 for control thereof in a manner to be described in greater detail below.

The first set of lighting devices 12 supported by the primary spindle hub 16 includes three (3) overhead lightheads 40-44, a surgical task light 46 and an operating room ambient light 48. Each of the surgical lightheads 40-44 are carried on a corresponding suspension system 40'-44'. Similarly, the surgical task light is carried on a suspension arm 46'. Each of the suspension arms 40'-46' carry appropriate power and communication cables which will be described below and further enable movement of the lightheads 40-44 and of the task light 46 into selected positions relative to the operating room application. Each lighthead is provided with a set of manually operable light intensity control buttons 124, preferably located adjacent the lighthead handle of each device. The ambient light 48 is mounted in a fixed location relative to the primary spindle hub 16. A single auxiliary lighthead 50 together with an auxiliary ambient light 52 is supported on the secondary spindle hub 20 by a suitable suspension arm 50'. It is to be appreciated that although several lighting devices are provided in the first set 12 and only a single lighting device is found in the second set 18, more or less lighting devices can be used as desired. Additionally, more or less spindle hubs 16, 20 can be included in the system as desired.

Figure 2A:
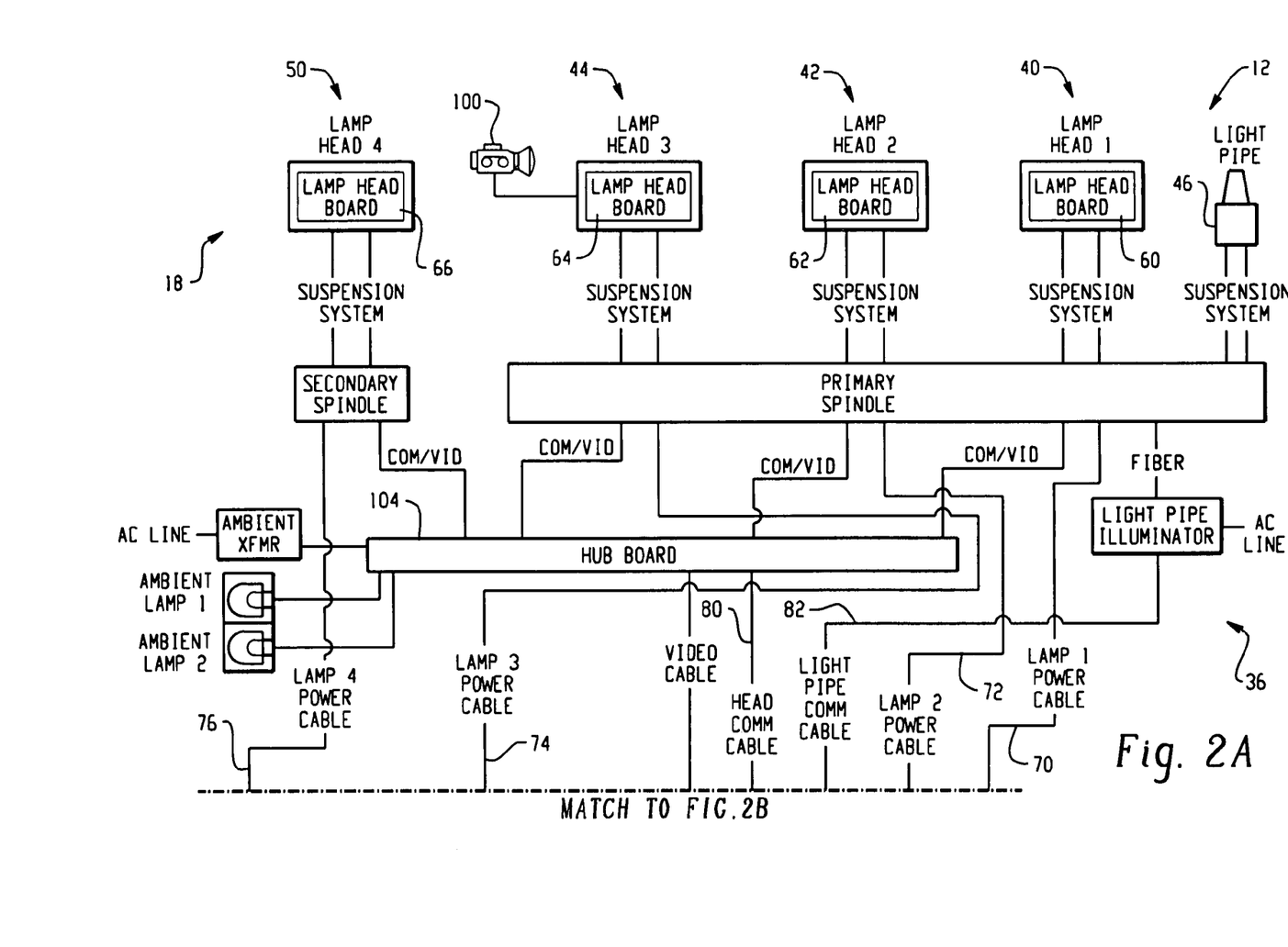
FIG. 2 is a block diagram illustrating components of the subject lighting control apparatus.
Figure 2B:
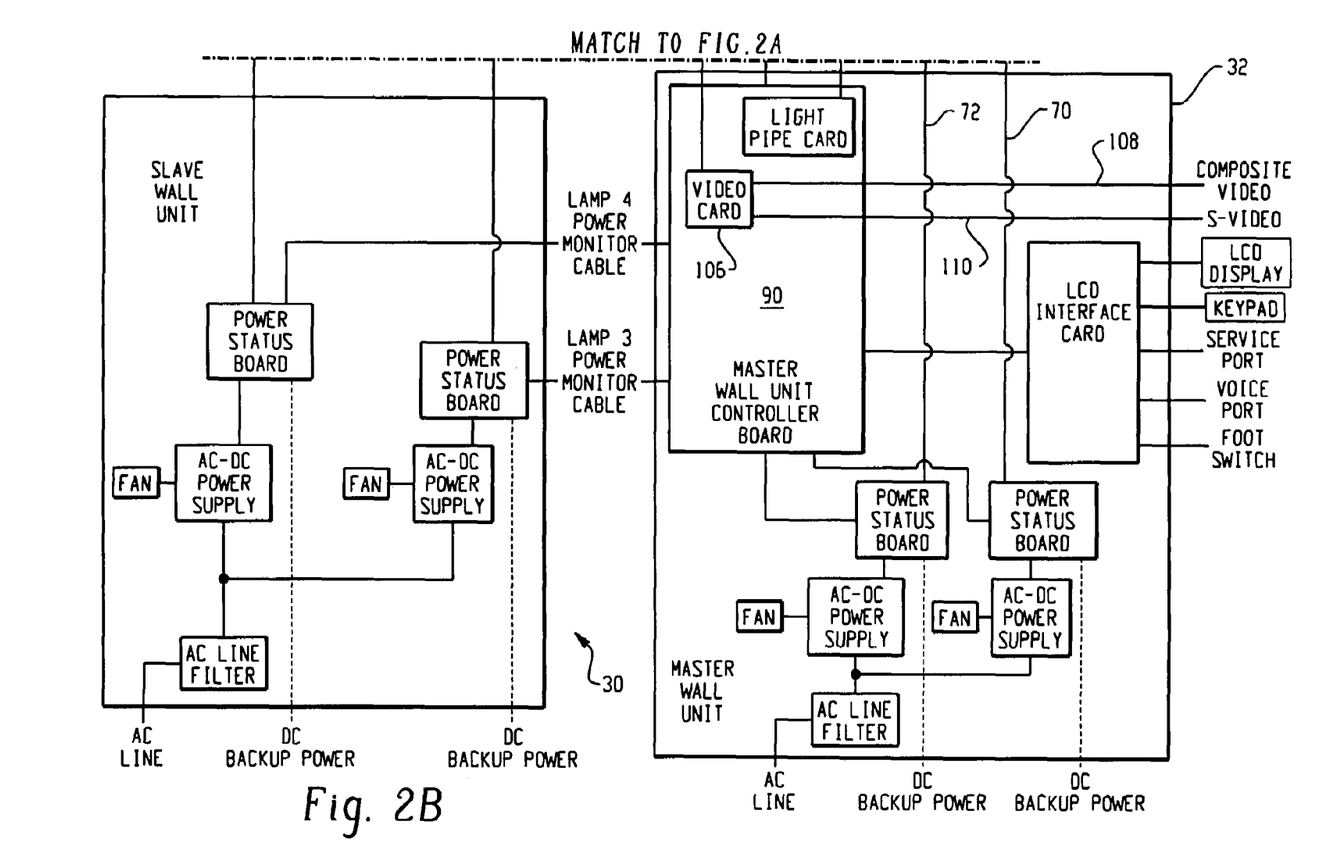

With reference next to FIG. 2, the subject lighting system 10 is shown in functional block diagram form. It is to be appreciated that the system is partitioned to provide a high level of redundancy to prevent single point failures from causing a "black out" or no light condition. To that end, each surgical lighthead includes a separate AC/DC power supply and further includes the capability to switch to a 24 VDC battery backup supply. Each surgical lighthead is also provided with its own electronics controller and resident operational firmware which is executable in the lighthead.

The lightheads 40-44 and 50 each respectively include an electronics module 60-66 for executing programs in accordance with predetermined algorithms. Each of the lightheads in the subject system are adapted to communicate with the lighting control apparatus 30 for controlling various lighting functions and to provide for plug and play capability. The communication and power lines 36 include separate lighthead power cables 70-76 for delivering power from the lighting control apparatus 30 to the individual lightheads. In addition, the communication and power lines 36 include a pair of communication cables 80, 82 for carrying command and status data between the lighting devices 12, 18 and the lighting control apparatus 30. To that end, the master control unit 32 includes an electronic controller board 90 for generating signals to be carried on the communication cables 80, 82 between the control unit and the lightheads 40-44, 50 and task light 46.

With continued reference to FIG. 2, it is to be noted that the embodiment of the subject surgical lighting system 10 includes a video camera 100. The video camera 100 is carried by the large lighthead 44 as illustrated. The video signals from the camera 100 pass through the suspension arm 44' of the large lighthead 44 and into a common hub electronics board 104 and into a video card component 106 of the electronic controller board 90 of the master control unit 32. The video card component 106 is adapted to generate a composite video signal 108 and an S-video signal 110.

Figure 3:
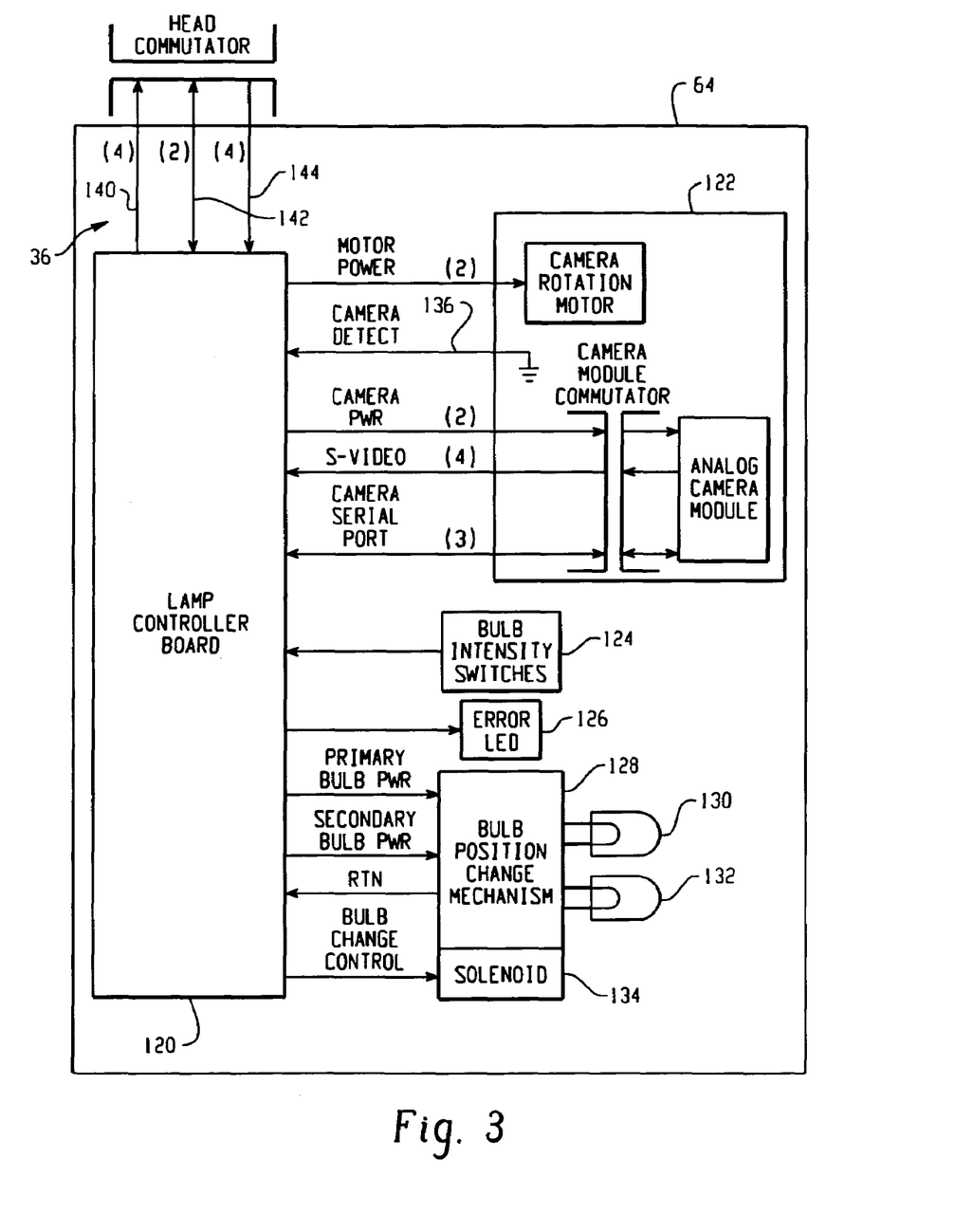
FIG. 3 is a block diagram illustrating functional blocks of an electronic module of the subject surgical lighting system.
Figure 4:
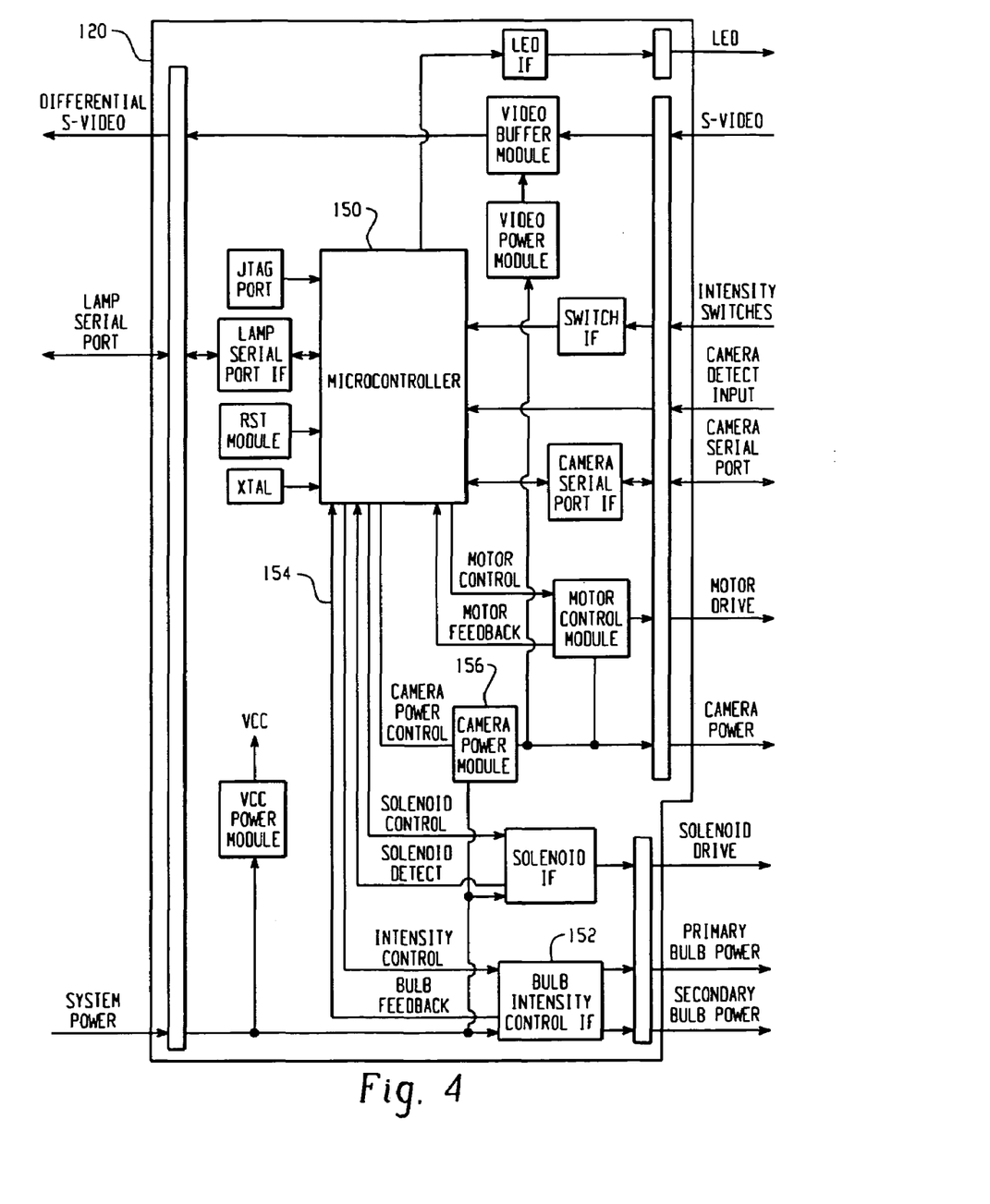
FIG. 4 is a functional block diagram illustrating a lamp controller board of the subject surgical lighting system.

FIGS. 3 and 4 show, in block diagram form, the functional components of the electronics module 64 of the large lighthead 44. As shown in FIG. 3, the electronics module 64 includes a lamp controller board 120, a camera module 122, a set of manually operable bulb intensity switches 124, a visual output lamp 126, preferably an LED, a bulb change mechanism 128 holding a primary 130 and a secondary 132 bulb, and a bulb change solenoid 134 for effecting bulb changes upon failure of the primary bulb 130. All of these components are in operative local communication with the lamp controller board 120. Operative communication with the lighting control apparatus 30 (FIGS. 1 and 2) is provided by the set of communication and power lines 36 including a differential video signal line 140, a lamp serial port signal line 142 and a system power signal line 144. The differential video signal line 140 delivers video signals from the camera module 122 to the lighting control apparatus 30. The lamp serial communication lines 142, however, are bi-directional and carry commands and data between the electronics module 64 and the lighting control apparatus 30. The system power lines 144 communicate electrical power to the lighthead.

Closed loop control is provided for lamp power. To that end, a bulb intensity controller 152 detects the current delivered to the bulb 130 and the voltage signal at the bulb terminal. A bulb feedback signal 154 is generated by the controller 152 and delivered to the microcontroller 150 or use in calculating a desired duty cycle for a PWM circuit 156. In this way, a consistent lighting effort is realized.

Further details of the lamp controller board 120 of the electronics module 64 is provided in FIG. 4. As shown, a microcontroller 150 is in operative communication with all of the components previously identified above. The microcontroller 150 is adapted to communicate with the lighting control apparatus in accordance with program code stored on a memory portion of the microcontroller. More particularly, the microcontroller 150 is adapted to execute program code to carry out the plug and play capabilities of the subject surgical lighting system.

The control system provides several levels of redundancy in order to minimize the potential loss of control of the lighting system during surgical procedures. Either one of the two power supplies in the control center is sufficient to maintain operation of the microcontroller. If the microcontroller or switches in the wall control unit fail, then ON/OFF and intensity control functionality can be performed using just the lighthead-based microcontroller and switches.

Figure 5:
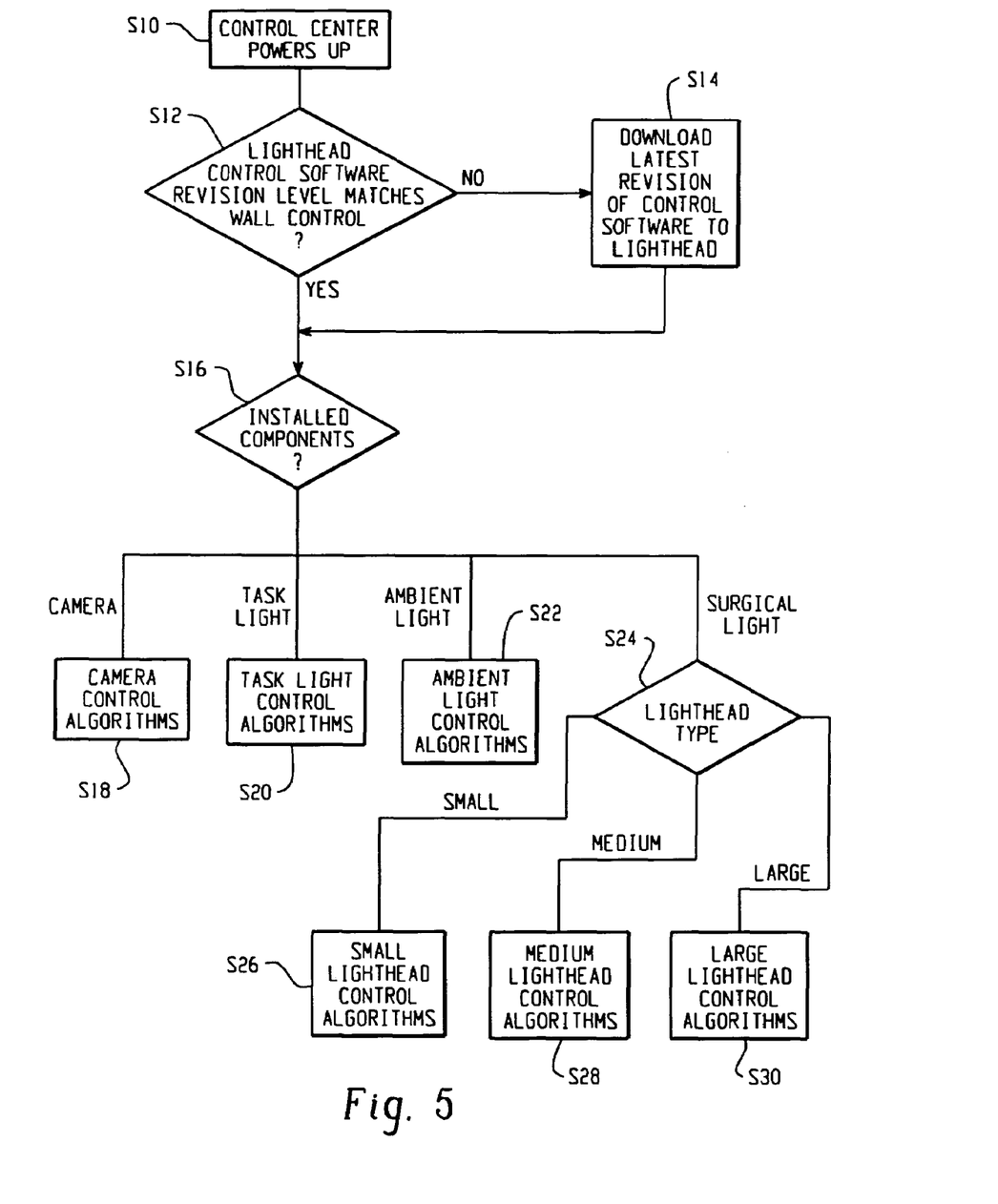
FIG. 5 is a flow chart illustrating a component auto-detect function executed by the subject control system.

FIG. 5 is a flowchart illustrating a device auto-detect sequence executed by the controller of the preferred embodiment. At power on S10, the lighting control apparatus 30 interrogates each of the microcontrollers 150 and each of the lightheads in order to determine a software revision level S12 and the quantity of lightheads in the system S16, their size and style, and any other information that can be derived at power up. One such determination is provided by a camera detect signal line 136 (FIG. 3) which is read by the microcontroller 150 of the lamp controller board 120 at power up. When a camera module 122 is installed in the electronics module 64, the camera detect signal line 136 is tied to a logical ground. In the absence of a camera module, the camera detect signal line 136 is permitted to float and represents a logical high value.

The microcontroller 150 includes program code to report the status of the presence of a camera module 122 within the electronics module 64 of the lighthead 44. Other information is also reported by the microcontroller 150 to the lighting control apparatus 30. This information includes data regarding the software version executed by the microcontroller 150. The subject surgical lighting system 10 uses this information beneficially to download new executable code to the microcontroller S14 when update software versions become available. To that end, the new software is downloaded S14 from the lighting control apparatus 30 to the separate electronics modules 60-66 using the communication and power lines 36.

Based upon a determination of the installed components S16, the controller selects an algorithm from among a group of algorithms for performing a control function. When a video camera is detected, a camera control algorithm is selected S18, a task light control algorithm and an ambient light control algorithm is selected at steps S20 and S22 when those devices are detected by the controller within the system. With regard to the surgical lightheads, as noted above, a variety of sizes are supported by the system, each preferably controlled according to separately distinct and tuned algorithms. To that end, the lighthead type is determined at step S24 and a small lighthead control algorithm is selected S26, a medium lighthead control algorithm is selected S28, and/or a large lighthead control algorithm is selected S30, based upon the lighthead type determination step S24.

Figure 6:
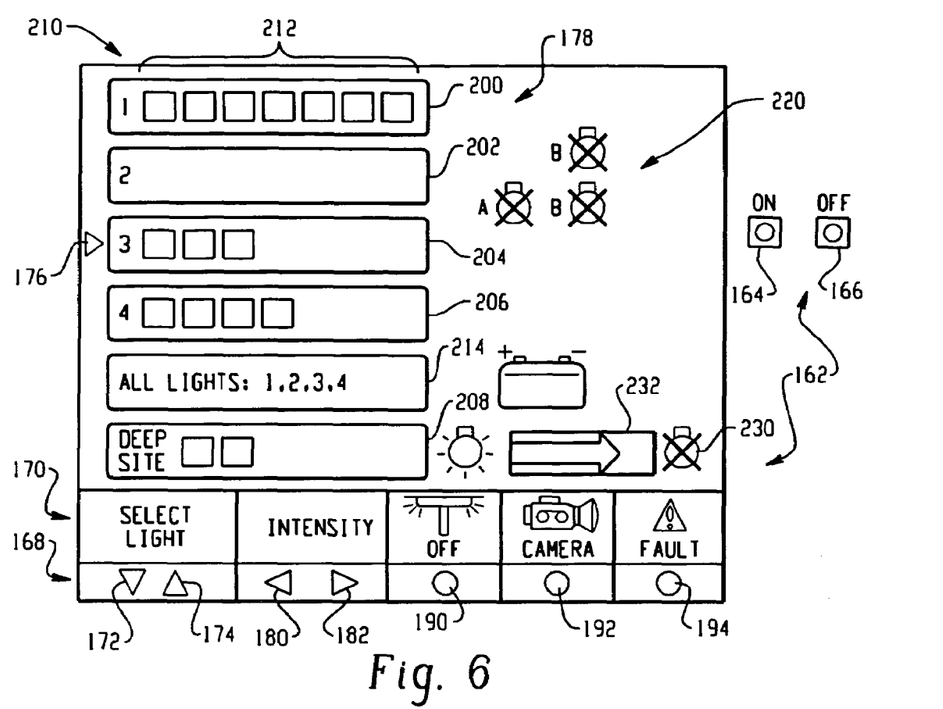
FIG. 6 is a view of a user's screen displayed by the lighting control apparatus of the subject surgical lighting.

FIG. 6 shows a user's display 160 presented on the master control unit 32 of the lighting control apparatus 30 of the subject surgical lighting system 10. Preferably, the master control unit includes a monochrome graphics LCD with backlight and a set of membrane contact switches 162. The contact switches 162 are used to obtain manual user input for controlling the subject surgical lighting system. An ON pushbutton 164 and an OFF push button 166 are provided together with a set of other control buttons 168 positioned adjacent a display area 170 which is programmed to solicit input from the user. The display area 170 essentially provides visual information to the human user regarding the function of the adjacent buttons 168. The visual information is generated by the software in the control and is useful to redefine the function of the physical buttons as needed.

As shown in FIG. 6, the display area 170 includes a "select light" indicia or label area, an "intensity" area, an "ambient light ON/OFF" area, a "camera" area, and a "system" area. An up arrow 172 and a down arrow 174 are provided among the other input buttons to select a lighthead from among the group. Actuation of either the up or down input buttons 172, 174 causes an arrow 176 displayed on the user display 160 to transition between one of three selectable fields 178. In addition, an intensity decrease arrow 180 and an intensity increase arrow 182 are provided for enabling the user at the lighting control apparatus 30 to control the intensity of the particular lighthead selected by the position of the arrow 176. As shown in FIG. 6, lighthead number 3 is selected by the arrow 176 and the intensity is set to level 3.

An ambient light power button 190 is also provided on the contact switches 162 together with an ambient light icon in the display area so that users can turn the ambient light 48 on or off as desired. A camera input button 192 is also provided adjacent a camera icon in the display area 170 for toggling camera operation. Lastly, a system inquiry button 194 is included for users to query the surgical lighting system for information.

A lighthead is selected using the UP/DOWN buttons 172, 174 under the SELECT LIGHT display, the intensity is adjusted with the LEFT/RIGHT buttons 180, 182 under the INTENSITY display. Seven (7) predefined power levels are hard coded into a non-volatile memory in the lighthead for each of the seven light intensity levels. The power level definitions for various wattage lamp types are stored in a set of power level tables in the lightheads. The intensity indicators 200-208 shown in FIG. 6, consist of a lamp head number 210 followed by a progressive, seven bar segment display 212. When the lamp is off, no segments are displayed. When the lamp is at a maximum intensity level, all seven segments are displayed. As shown in the FIGURE, lamp 1 is at full power, lamp 2 is off, lamp 3 is at a low power setting, and lamp 4 is slightly brighter than lamp 3. As the user increases lamp intensity, successive segments are displayed from left to right with all preceding segments remaining on.

When two or more lightheads are detected in the system, the ALL LIGHTS indicator 214, shown in the FIGURE are displayed on the light control screen. When the ALL LIGHTS indicator is selected using the UP/DOWN buttons 172, 174 under the SELECT LIGHT display, the control and intensity of all detected lightheads follows a predefined operational sequence. Essentially, when the ALL LIGHTS indicator is selected and the intensity right 182 or up button is selected, all lamps immediately increase to the next higher level of intensity. Conversely, when the left 180 or down arrow is pressed, all lamps in the system immediately decrease in intensity to the next lower level.

Primary and secondary lamps for the lighthead are designated as "A" and "B" with the "A" being understood as the primary lamp location. In the system of the preferred embodiment as noted above, the lamps are continuously monitored regardless of whether they are turned ON or OFF. When a lamp is missing or burned out, a lamp fault indicator 220 is displayed and flashes on and off at a preselected rate, preferably a two second rate with a fifty percent duty cycle.

With continued reference to the drawing figures, the system automatically detects the installation of a manual task light as described above. To that end, a task light intensity display 208 is provided together with a lamp life indicator 230. The intensity indicator consists of a seven segment display 212 in the form of a bar graph similar to the display provided for the lightheads. As the user increases lamp intensity, successive segments are displayed from left to right with all preceding segments remaining on.

In addition, a task light lamp life indicator 230 is presented to the operator to indicate the remaining life on the lamp used in the manual task light. A progress bar meter 232 moves to the right as shown in the drawing figure as lamp light diminishes. The bar is calibrated preferably for 0 hours on the left and 500 hours full scale on the right. After the bar graph reaches 400 hours of bulb life, the progress bar begins to flash at a predetermined rate, preferably a two second rate with a fifty percent duty cycle. After 500 hours are reached, a graphical display of a lamp with a cross therethrough is indicated and begins flashing to attract the attention of the operator. At 500 hours, a fault log entry is made which indicates that the number of lamp hours used in the manual task light has exceeded a predetermined operational limit.

In addition, a backup battery display icon is presented to display the remaining life of the backup battery.

Figure 7:
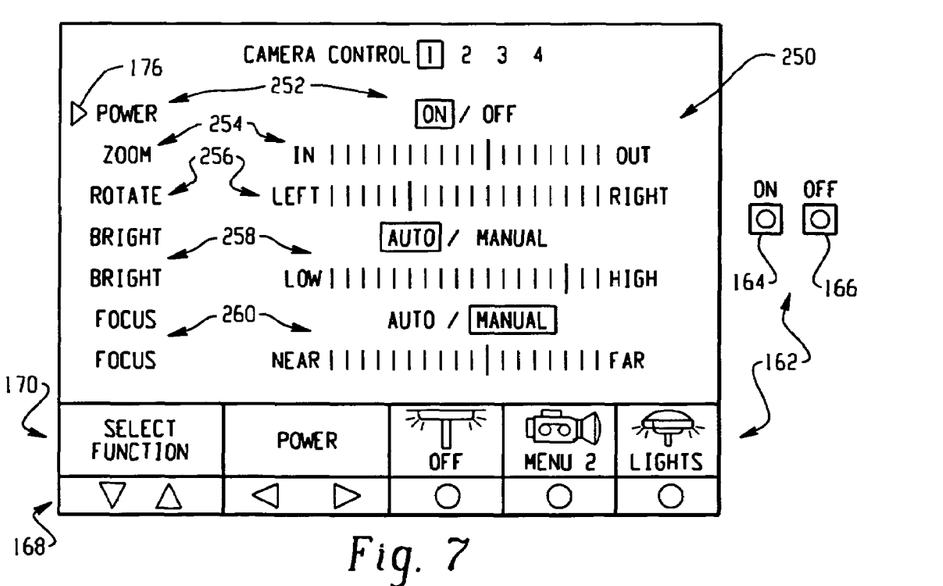
FIG. 7 is a view of the user's screen displaying a sub-menu provided by the lighting control apparatus of the subject system.

FIG. 7 shows a sub-menu 250 presented by the subject control system when the button below the "camera" icon 234 (FIG. 6) is operated. As shown, select function keys 172, 174 are used to change the position of an arrow 176 to select various camera control options including power 252, zoom 254, rotate 256, a brightness adjustment 258, and a camera focus 260.

Having thus described the preferred embodiments, the invention is now claimed to be:

1. A surgical light system comprising:
   a lighthead coupled to a suspension arm adapted for mounting to a surface of a surgical room;
   a bulb in said lighthead;
   a processor in said lighthead operatively coupled with the bulb for controlling an intensity of light of the bulb and being adapted to generate a lighthead status signal representative of a first status of said lighthead; and
   a control apparatus configured to control said lighthead and being in operative communication with said processor in said lighthead, the control apparatus i) receiving said lighthead status signal and ii) selecting a set of executable software code control algorithms from among a group of executable software code control algorithms based on said lighthead status signal, the control apparatus controlling said lighthead by executing the selected set of executable software code control algorithms.

2. The surgical light system according to claim 1 wherein said first status of said lighthead includes a least a one of:
   a size of said lighthead;
   an intensity of light from said bulb;
   a condition of said bulb;
   a level of current applied to said bulb;
   a level of voltage applied to said bulb;
   an internal temperature of said lighthead;
   a presence of a video camera;
   a presence of a manual surgical task light; and,
   a presence of a controllable ambient light.

3. The surgical light system according to claim 1 wherein:
   said control apparatus is adapted to generate a query signal; and,
   the processor is adapted to generate said lighthead status signal in response to said query signal.

4. The surgical light system according to claim 3 further including a serial data communication link for carrying said query signal and said lighthead status signal between said processor and said control apparatus.

5. The surgical light system according to claim 4 wherein said control apparatus includes an LCD display for displaying said first status.

6. The surgical light system according to claim 1 wherein:
   the control apparatus is adapted to generate a command signal; and,
   the processor in the lighthead is adapted to control the intensity of light in accordance with the command signal.

7. The surgical light system according to claim 1 wherein said processor in said lighthead is adapted to:
   receive computer executable software code from said control apparatus; and,
   execute said computer executable software code.

8. The surgical light system according to claim 7 wherein said control apparatus is adapted to i) determine an operational compatibility of said processor in said surgical light system based on said lighthead status signal received; and, ii) when the processor is not compatible for use in the surgical light system, download said executable program code to the processor.

9. The surgical light system according to claim 1 further including a camera associated with said lighthead and operatively coupled with said control apparatus, the camera generating an image signal adapted for conversion by an associated video monitor device to a human readable image, the control apparatus including means for controlling functions of said camera including white balance, picture freeze, time display, and date display.

10. The surgical light system according to claim 9 wherein the control apparatus is adapted to detect a presence of said camera and route said image signal to a port on the control apparatus adapted for connection to the associated video monitor device.

11. The surgical light system according to claim 1 further including:
- a first light intensity control button on said lighthead and a second light intensity control button on said control apparatus, said processor being responsive to both said first and second light intensity control buttons.

12. The surgical light system according to claim 1 further including a surgical video camera device adapted to generate a video signal, wherein:
- said processor in said lighthead is adapted to generate a video camera present signal; and,
- said control apparatus is adapted to receive the video camera present signal and select a camera control algorithm from said group of algorithms for controlling said surgical video camera device.

13. The surgical light system according to claim 12 further including a human readable display for displaying information relating to said lighthead status signal and to said video camera device.

14. A surgical light system comprising:
- a lighthead coupled to a suspension arm adapted for mounting to a surface of a surgical room;
- a bulb in said lighthead;
- a processor in said lighthead operatively coupled with the bulb for controlling an intensity of light of the bulb and being adapted to generate a lighthead status signal representative of a software version of executable software code executed by the processor in the lighthead; and,
- a control apparatus configured to control said lighthead and being in operative communication with said processor in said lighthead, the control apparatus receiving said lighthead status signal and selecting a set of control algorithms from among a group of algorithms based on said lighthead status signal for controlling said lighthead using the selected set of control algorithms, said control apparatus being adapted to selectively download updated executable software code to said lighthead for execution by said processor in said lighthead based on said status signal.

15. The surgical light system according to claim 14 wherein said control apparatus is adapted to compare said software version of executable software code executed by the processor in the lighthead with a second software version of executable software code executed by the control apparatus.

16. The surgical light system according to claim 15 wherein said updated executable software code is downloaded from said control apparatus to said processor in said lighthead when said software version of executable software code executed by the processor in said lighthead does not match said second software version of executable software code in said control apparatus.

* * * * *